US00PP34966P2

(12) United States Plant Patent
Kolster et al.

(10) Patent No.: US PP34,966 P2
(45) Date of Patent: Feb. 7, 2023

(54) ***HYDRANGEA* PLANT NAMED 'HOKOPINEL'**

(50) Latin Name: *Hydrangea macrophylla*
Varietal Denomination: Hokopinel

(71) Applicants: Kolster Holding B.V., Boskoop (NL); Horteve Breeding B.V., Aalsmeer (NL)

(72) Inventors: Peter Rudolf Kolster, Boskoop (NL); Cornelis Pieter Eveleens, Aalsmeer (NL)

(73) Assignees: KOLSTER HOLDING BV, Boskoop (NL), part interest; HORTEVE BREEDING BV, Aalsmeer (NL), part interest ( * ) Notice: Subject to any disclaimer, the term of this patent is extended or adjusted under 35 U.S.C. 154(b) by 0 days.

(21) Appl. No.: 17/857,141

(22) Filed: Jul. 4, 2022

(30) Foreign Application Priority Data

Jul. 21, 2021 (QZ) ..... PBR 20211907

(51) Int. Cl.
*A01H 6/48* (2018.01)
*A01H 5/02* (2018.01)

(52) U.S. Cl.
USPC ..... Plt./250

(58) Field of Classification Search
USPC ..... Plt./250
See application file for complete search history.

*Primary Examiner* — Annette H Para
(74) *Attorney, Agent, or Firm* — Penny J. Aguirre

(57) ABSTRACT

A new cultivar of *Hydrangea macrophylla* plant named 'Hokopinel' that is characterized by its very floriferous blooming habit, its clear pink inflorescences that perform well under bluing conditions, its compact and upright plant habit, its suitability as a potted plant, and its high resistance to *Botrytis* in cold storage.

3 Drawing Sheets

Botanical classification: *Hydrangea macrophylla.*
Varietal denomination: 'Hokopinel'.

CROSS-REFERENCE TO A RELATED APPLICATION

This application claims priority to European Community Plant Variety Office (CPVO) Plant Breeder's Rights Application No. 2021/1907 filed on Jul. 21, 2021, under 35 U.S.C. 119(f), the entire contents of which is incorporated by reference herein.

BACKGROUND OF THE INVENTION

The present invention relates to a new and distinct cultivar of *Hydrangea macrophylla* and will be referred to hereafter by its cultivar name, 'Hokopinel'. 'Hokopinel' represents a new bigleaf *Hydrangea*, a perennial shrub grown for use in the landscape and as a potted plant.

'Hokopinel' derived from an ongoing controlled breeding program directed by the Inventors. An objective of the breeding program included developing a new cultivar of *Hydrangea* with clear pink inflorescences that can also be grown under bluing conditions combined with a floriferous blooming habit.

'Hokopinel' arose from a controlled cross made by the Inventors in Boskoop, The Netherlands in June of 2007 between an unnamed and unpatented proprietary plant in the Inventor's breeding program (reference no. 05-012-014) as the female parent and an unnamed and unpatented proprietary plant in the Inventor's breeding program (reference no. 06-008-003) as the male parent. The new cultivar was selected as a single unique plant in June of 2009.

Asexual propagation of the new cultivar was first accomplished by stem cuttings by one of the Inventors in August of 2009 in Boskoop, The Netherlands. Asexual propagation by stem cuttings has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Hokopinel' as a unique cultivar of *Hydrangea macrophylla.*

1. 'Hokopinel' exhibits a very floriferous blooming habit.
2. 'Hokopinel' exhibits clear pink inflorescences that perform well under bluing conditions.
3. 'Hokopinel' exhibits large mophead inflorescences.
4. 'Hokopinel' exhibits a compact and upright plant habit.
5. 'Hokopinel' exhibits suitability as a potted plant.
6. 'Hokopinel' exhibits high resistance to *Botrytis* in cold storage.

The female parent of 'Hokopinel' differs from 'Hokopinel' in having inflorescences that are smaller in size and lighter pink in color and leaves that are lighter green in color. The male parent of 'Hokopinel' differs from 'Hokopinel' in having leaves that are smaller in size, branches that are thinner, and individual sterile flowers that are smaller in size. 'Hokopinel' can be most closely compared to the *Hydrangea macrophylla* cultivars 'Anda' (not patented) and 'Rosita' (not patented). 'Anda' is similar to 'Hokopinel' in having inflorescences that are pink in color, sterile flowers that are large in size, and in being suitable for growing as a potted plant. 'Anda' differs from 'Hokopinel' in having inflorescences that are smaller in size and less branching and in being more sensitive to *Botrytis* during cold storage. 'Rosita' is similar to 'Hokopinel' in having inflorescences that are pink in color and in being suitable for growing as a potted plant. 'Rosita' differs from 'Hokopinel' in having less branches that are thinner and weaker (needs support).

BRIEF DESCRIPTION OF THE DRAWINGS

The accompanying color photographs illustrate the overall appearance and distinct characteristics of the new *Hydrangea*.

The photographs in FIG. 1, FIG. 2 and FIG. 3 were taken of an 18-month-old plant of 'Hokopinel' as grown outdoors in a greenhouse in a 1-gallon container in Loxley, Ala.

Figure 1:
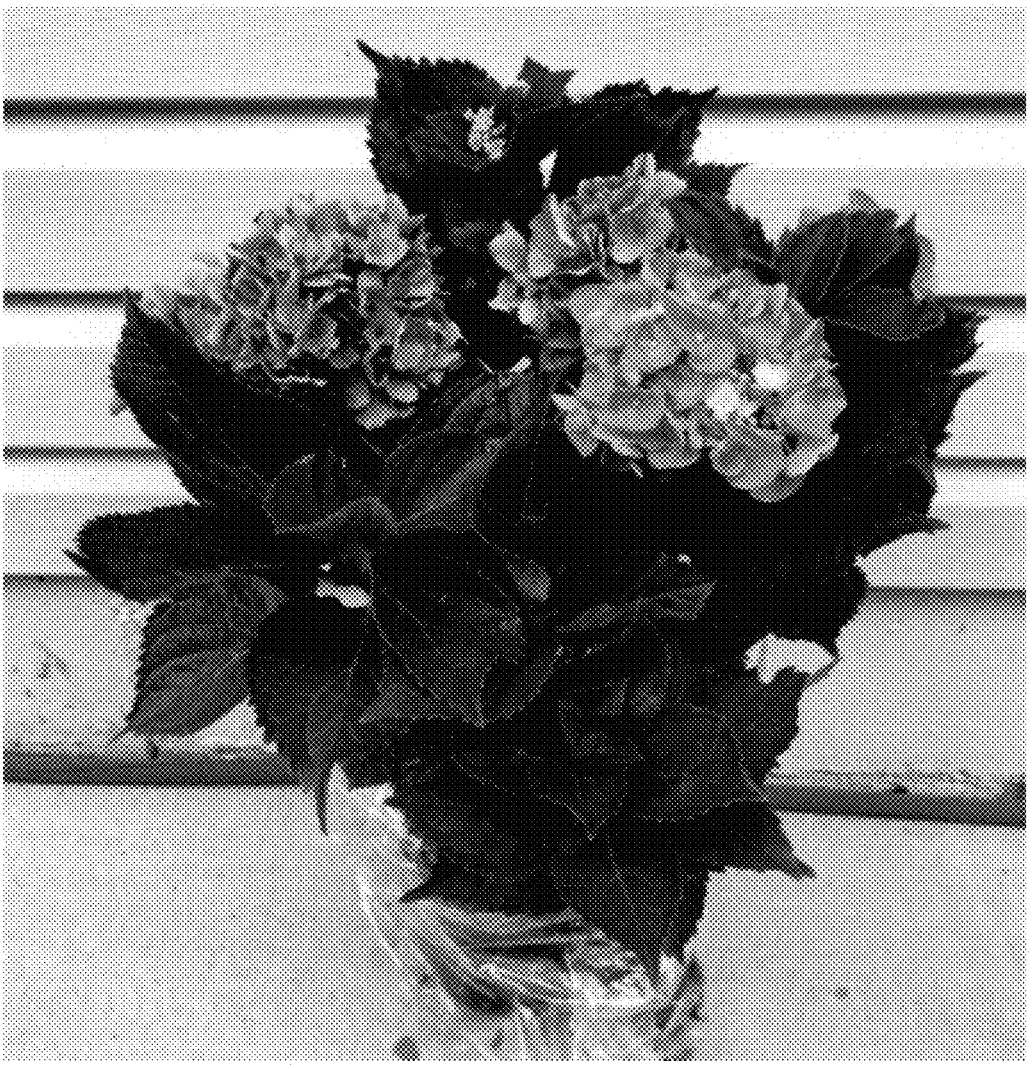

The photograph in FIG. 1 provides a side view of the plant habit of 'Hokopinel' in bloom.

Figure 2:
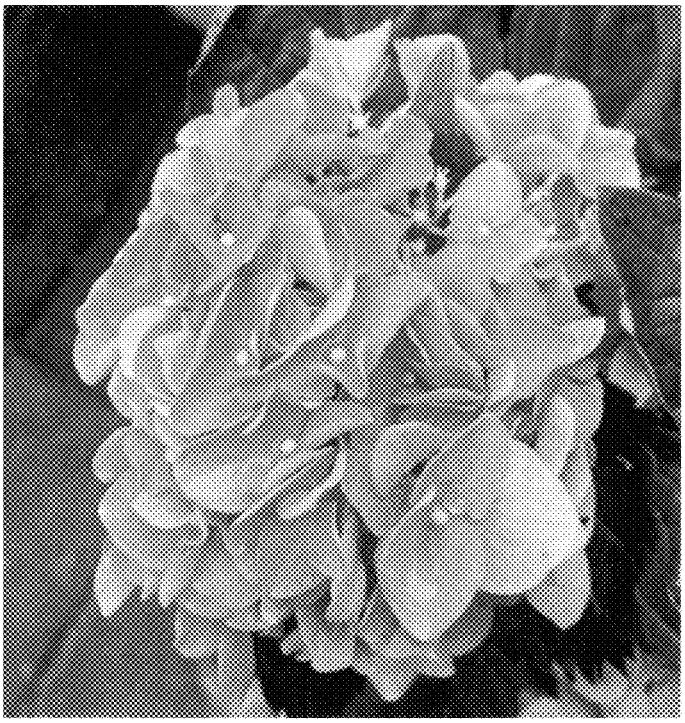

The photograph in FIG. 2 provides a close-up view of a fully open inflorescence of 'Hokopinel'.

Figure 3:
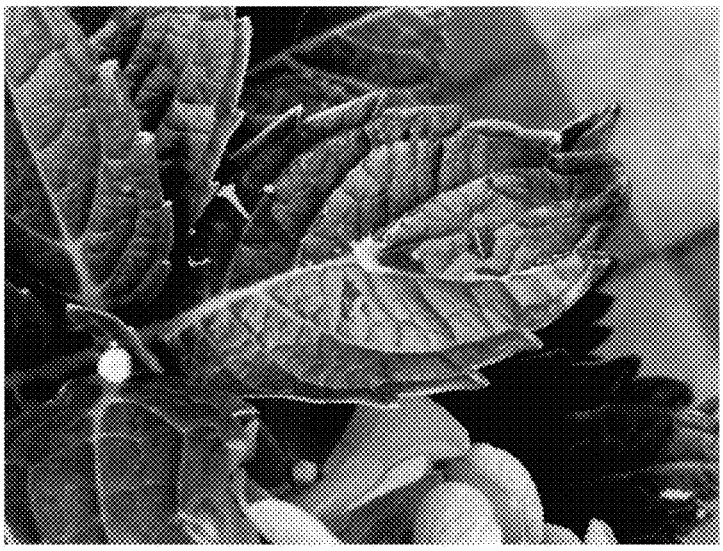

The photograph in FIG. 3 provides a close-up view of the foliage of 'Hokopinel'.

Figure 4:
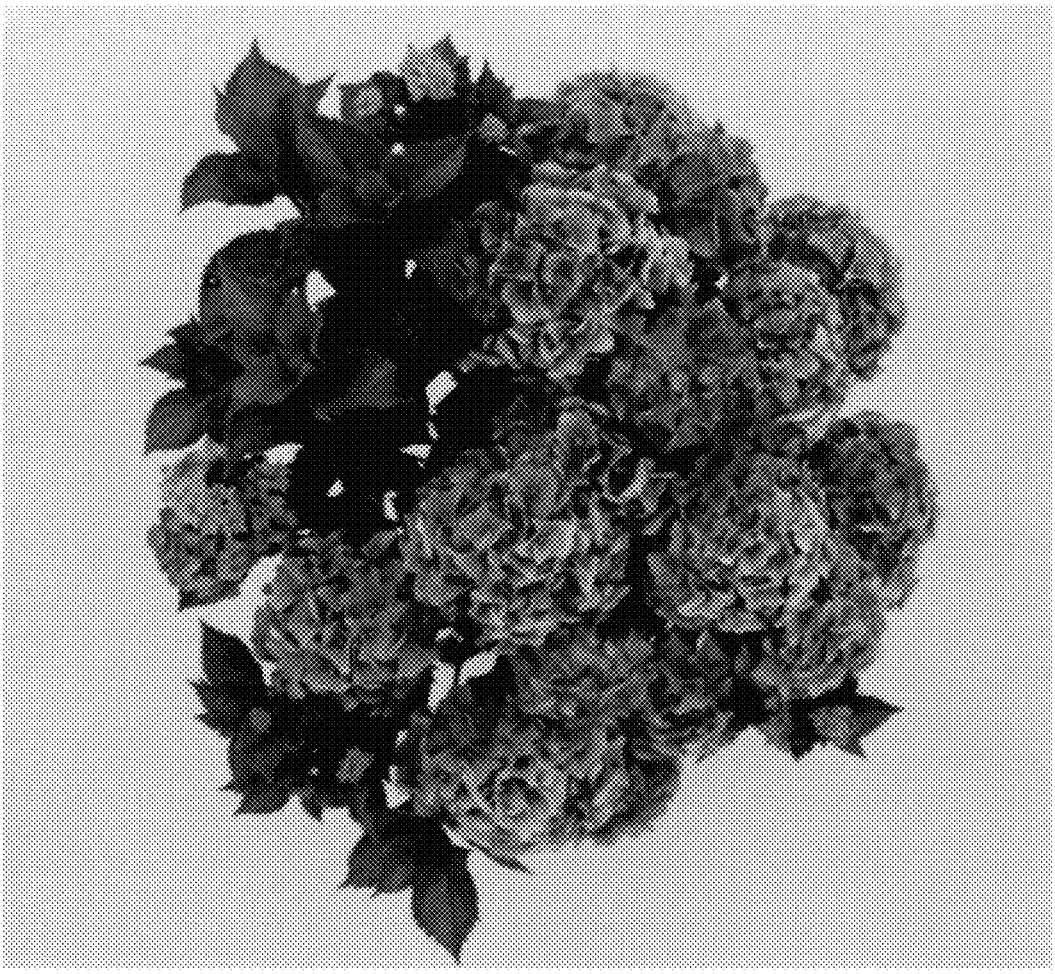

The photograph in FIG. 4 was taken of a 2-year-old plant of 'Hokopinel' as grown in a greenhouse in a 5-liter container in Boskoop, The Netherlands and provides a view of a plant of 'Hokopinel' subject to bluing by growing the plant with sufficient aluminum sulfate and a soil pH of <6.5.

The colors in the photographs are as close as possible with the photographic and printing technology utilized and the color values cited in the detailed botanical description accurately describe the colors of the new *Hydrangea*.

BOTANICAL DESCRIPTION OF THE PLANT

The following is a detailed description of 18-month-old plants of 'Hokopinel' as grown in a greenhouse in 1-gallon containers in Loxley, Ala. and grown under non-bluing conditions (with exception of bluing sterile sepal color). The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period.*—Late spring to late summer in The Netherlands with flowers showy at least for 2 months.

*Plant type.*—Deciduous shrub, mophead type *Hydrangea*.

*Plant habit.*—Upright, compact.

*Height and spread.*—An average of 40 cm in in height and 32 cm in spread as an 18-month-old plant and 1 m in height and width as a 3-year-old plant in the garden.

*Hardiness.*—At least in U.S.D.A. Zones 6 to 9.

*Diseases and pests.*—Exhibiting high resistance to *Botrytis* sp. during cold storage, no susceptibility and resistance to pests has been observed.

*Root description.*—Fine and fibrous, 161C in color.

*Propagation.*—Stem cuttings.

*Root development.*—An average of 6 weeks for root initiation with a young rooted plant produced in an average of 18 weeks.

*Growth rate and vigor.*—Moderate.

Branch description:

*Branch shape.*—Rounded.

*Branch strength.*—Strong.

*Branch color.*—Young; 145A, mature; 144A, older woody branches and bark; N199A and N199B.

*Branch size.*—Main branches; an average of 7 cm in length and 7 mm in diameter, lateral branches; average of 18 cm in length and 4 mm in diameter.

*Branch surface.*—Young and mature; glossy, glabrous, branches are sparsely covered with lenticels; oval in shape, average of 7 per 1 cm diameter, average of 1 mm in length, 0.2 mm in width, 200A in color, older woody branches and old bark; exfoliating, matte, dry, fasciation absent.

*Branch aspect.*—Upright to slightly outward.

*Internode length.*—An average of 4 cm.

*Branching.*—Freely branching; 3 main branches, 4 lateral branches per main branch.

Foliage description:

*Leaf shape.*—Ovate to broadly ovate.

*Leaf arrangement.*—Opposite.

*Leaf division.*—Simple.

*Leaf base.*—Short attenuate.

*Leaf apex.*—Short apiculate.

*Leaf margins.*—Serrate.

*Leaf venation.*—Pinnate, color; upper and lower surface 145D.

*Leaf size.*—An average of 10.5 cm in length and 7 cm in width.

*Leaf attachment.*—Petiolate.

*Leaf number.*—An average of 12 per lateral stem.

*Leaf surface.*—Upper surface; glabrous, matte with a slight sheen, lower surface glabrous, matte.

*Leaf color.*—Young foliage upper and lower surface 150B, mature foliage upper surface 146A and 143A, mature foliage lower surface N148A and 143D.

*Petioles.*—An average of 1 cm in length and 3 mm in diameter, upper and lower surface color 149D, both surfaces are smooth and slightly glossy.

Inflorescence description:

*Inflorescence type.*—Terminal panicle, flattened mophead comprised of a sterile flowers above fertile flowers.

*Lastingness of inflorescence.*—Sterile flowers; persistent for an average of 6 weeks, fertile flowers; self-cleaning, an average of 5 days.

*Inflorescence number.*—One per lateral stem.

*Inflorescence size.*—An average of 10 cm in height and 15 cm in diameter.

*Flower number.*—An average of 150 sterile flowers and 250 fertile flowers per panicle.

*Flower fragrance.*—None.

*Flower aspect.*—Upright to outward.

*Flower size.*—Sterile flowers; an average of 3 cm in diameter and 1.5 cm in depth, fertile flowers; buds fall after maturing, do not open.

*Flower type.*—Rotate.

*Flower buds.*—Sterile and fertile flowers; an average of 2 mm in length and diameter, round and slightly flattened in shape, 157A in color.

*Peduncles.*—Strong, flattened oval in shape, an average of 2 cm in length and 3 mm in width, 144B in color, moderately covered with lenticels; linear and thin in shape, average of 5 per 1 cm diameter, average of 0.5 mm in length and width, 200B in color, surface is glossy.

*Pedicels.*—Strong, rounded in shape, an average of 1 cm in length and 2 mm in width, color; young pedicels 73D and 73A, mature pedicels 144B, flushed with 69C, 75A and N75A, moderately covered with lenticels; linear and thin in shape, average of 18 per 1 cm diameter, average of 2 mm in length, 0.5 mm in width, 200B in color, surface is glossy.

*Petals.*—Petals do not open, sterile flowers mature petal spot; 2 mm in diameter, 1.3 mm in depth, rounded and flattened in shape, NN155C in color, fertile flowers mature petal spot; 3 mm in diameter and depth, rounded in shape, 155A.

*Sepals.*—Sterile flowers; 4, rotate, apex is broadly and bluntly acute, some have emarginate tips, base is broadly cuneate, margins are undulate and sometimes serrated on the outer center section, reniform to nearly deltoid in shape, an average of 2 cm in length and 3 cm in width, upper and lower surface glabrous, velvety and matte, color; when opening upper and lower surface; at burst 11D, as the sepals open becoming flushed with N87D, when fully open upper and lower surface a blend of 68A, 67A and 67D, then as the sepal matures, changing to a blend of 75A and 97B, when grown under bluing conditions both surfaces are a blend of primarily 86D, N88C, and 91B to 91C, fertile flowers; 5, triangular and very small, 0.3 mm in length and width, acute apex, cuneate base, both surfaces glabrous and glossy, 18B in color.

Reproductive organs:

*Presence.*—Not observed, flowers do not open; sterile and fertile flowers (petal spot) drop after flower bud matures, leaving 3 under-developed pistils, 1.5 mm in length, stigma; round in shape, 0.5 mm in diameter, NN155C in color, style; 1 mm in length, 0.3 mm in diameter, NN155C in color, ovary inferior, round in shape, 0.5 mm in diameter, 155C in color, moderately covered with thin, translucent woolly hairs.

*Fruit and seed.*—Not observed.

It is claimed:

1. A new and distinct cultivar of *Hydrangea* plant named 'Hokopinel' substantially as herein illustrated and described.

* * * * *